(12) United States Patent
Kwack et al.

(10) Patent No.: US 9,879,035 B2
(45) Date of Patent: Jan. 30, 2018

(54) COMPOSITION FOR FABRICATING ORGANIC FILM, ORGANIC LIGHT-EMITTING DISPLAY APPARATUS MANUFACTURED USING THE SAME, AND METHOD OF MANUFACTURING THE ORGANIC LIGHT-EMITTING DISPLAY APPARATUS

(71) Applicant: SAMSUNG DISPLAY CO., LTD., Yongin, Gyeonggi-Do (KR)

(72) Inventors: Jinho Kwack, Yongin (KR); Seungyong Song, Yongin (KR); Taewook Kang, Yongin (KR); Youngseo Choi, Yongin (KR); Changmok Kim, Yongin (KR); Daebeom Shin, Yongin (KR); Yonghyuck Lee, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 332 days.

(21) Appl. No.: 14/707,750

(22) Filed: May 8, 2015

(65) Prior Publication Data
US 2016/0137769 A1   May 19, 2016

(30) Foreign Application Priority Data
Nov. 19, 2014   (KR) .................... 10-2014-0161624

(51) Int. Cl.
*H01L 29/08*   (2006.01)
*C09K 3/00*   (2006.01)
(Continued)

(52) U.S. Cl.
CPC ............ *C07F 7/1804* (2013.01); *C07C 69/54* (2013.01); *C08F 222/1006* (2013.01);
(Continued)

(58) Field of Classification Search
CPC ......... C07C 69/54; C07F 7/1804; C09D 4/00; C09D 133/10; C08F 222/1006; C08F 2222/1013; C08F 220/30; H01L 51/5256
(Continued)

(56) References Cited

U.S. PATENT DOCUMENTS

2003/0203210 A1   10/2003   Graff et al.
2008/0006819 A1   1/2008   McCormick et al.
(Continued)

FOREIGN PATENT DOCUMENTS

EP   2 708 580   3/2014
KR   10-2009-0018825 A   2/2009
(Continued)

OTHER PUBLICATIONS

Extended European Search Report dated Mar. 18, 2016 for EP 15182794.6; Kwack, et al.

*Primary Examiner* — William Cheung
(74) *Attorney, Agent, or Firm* — Lee & Morse, P.C.

(57) ABSTRACT

A composition for fabricating an organic film, an organic light-emitting display apparatus manufactured using the same, and a method of manufacturing the organic light-emitting display apparatus, the composition comprising a first compound that includes n substituents Y, and m polymerizable groups $P_1$, wherein n is selected from 1, 2, 3, and 4; m is selected from 1, 2, 3, and 4; $OP_1$ of the first compound is equal to or greater than 2.8 and equal to or less than 4.8; $OP_1$ being (total number of atoms of the first compound)/{(number of carbon atoms of the first compound)−(number of oxygen atoms of the first compound)}; and $RP_1$ of the first compound is equal to or greater than 0.01 and equal to or less than 0.46; $RP_1$ being {(number of carbon atoms of the substituent Y)X n}/(number of carbon atoms of the first compound).

17 Claims, 1 Drawing Sheet

(51) Int. Cl.
*H01L 21/00* (2006.01)
*C08F 222/10* (2006.01)
*C07F 7/04* (2006.01)
*C07C 69/34* (2006.01)
*C07C 69/52* (2006.01)
*C07F 7/18* (2006.01)
*C07C 69/54* (2006.01)
*C09D 4/00* (2006.01)
*C08F 230/08* (2006.01)
*C09D 133/10* (2006.01)
*H01L 51/52* (2006.01)

(52) U.S. Cl.
CPC .............. *C08F 230/08* (2013.01); *C09D 4/00* (2013.01); *C09D 133/10* (2013.01); *H01L 51/5256* (2013.01)

(58) Field of Classification Search
USPC ......... 257/40; 252/182.18; 438/26; 526/325; 556/442; 560/201, 221
See application file for complete search history.

(56) References Cited

U.S. PATENT DOCUMENTS

| | | |
|---|---|---|
| 2012/0133275 A1 | 5/2012 | Lee et al. |
| 2012/0146492 A1 | 6/2012 | Ryu et al. |
| 2012/0256201 A1 | 10/2012 | Lee et al. |
| 2013/0245756 A1* | 9/2013 | Liao ...................... A61F 2/1648 623/6.56 |
| 2014/0048780 A1 | 2/2014 | Song et al. |
| 2014/0070195 A1 | 3/2014 | Choi et al. |
| 2014/0145154 A1* | 5/2014 | Kim .................... H01L 51/5256 257/40 |

FOREIGN PATENT DOCUMENTS

| | | |
|---|---|---|
| KR | 10-2012-0057286 A | 6/2012 |
| KR | 10-2012-0065049 | 6/2012 |
| KR | 10-2012-0113555 A | 10/2012 |
| KR | 10-2014-0008215 A | 1/2014 |
| KR | 10-2014-0024987 A | 3/2014 |

* cited by examiner

COMPOSITION FOR FABRICATING ORGANIC FILM, ORGANIC LIGHT-EMITTING DISPLAY APPARATUS MANUFACTURED USING THE SAME, AND METHOD OF MANUFACTURING THE ORGANIC LIGHT-EMITTING DISPLAY APPARATUS

CROSS-REFERENCE TO RELATED APPLICATION

Korean Patent Application No. 10-2014-0161624, filed on Nov. 19, 2014, in the Korean Intellectual Property Office, and entitled: "Composition For Fabricating Organic Film, Organic Light-Emitting Display Apparatus Manufactured Using The Same, and Method Of Manufacturing The Organic Light-Emitting Display Apparatus," is incorporated by reference herein in its entirety.

BACKGROUND

1. Field

Embodiments relate to compositions for fabricating an organic film, organic light-emitting display apparatuses manufactured using the same, and methods of manufacturing the organic light-emitting display apparatuses.

2. Description of the Related Art

Organic light-emitting devices, which are self-emitting devices, have advantages such as wide viewing angles, excellent contrast, quick response, high brightness, and excellent driving voltage characteristics, and can provide multicolored images.

An organic light-emitting device may have a structure including a substrate, and a first electrode, a hole transport region, an emission layer, an electron transport region, and a second electrode, which are sequentially disposed on the substrate. Holes injected from the first electrode move to the emission layer via the hole transport region, and electrons injected from the second electrode move to the emission layer via the electron transport region. Carriers such as the holes and electrons recombine in the emission layer to generate excitons. When the excitons drop from an excited state to a ground state, light is emitted.

SUMMARY

Embodiments are directed to compositions for fabricating an organic film, organic light-emitting display apparatuses manufactured using the same, and methods of manufacturing the organic light-emitting display apparatuses.

The embodiments may be realized by providing a composition for fabricating an organic film, the composition including a first compound that includes n substituents Y, and m polymerizable groups $P_1$, wherein n is selected from 1, 2, 3, and 4; m is selected from 1, 2, 3, and 4; $OP_1$ of the first compound is equal to or greater than 2.8 and equal to or less than 4.8; $OP_1$ being (total number of atoms of the first compound)/{(number of carbon atoms of the first compound)−(number of oxygen atoms of the first compound)}; and $RP_1$ of the first compound is equal to or greater than 0.01 and equal to or less than 0.46; $RP_1$ being {(number of carbon atoms of the substituent Y)X n}/(number of carbon atoms of the first compound).

Y may be selected from a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group.

m may be selected from 1, 2, and 3.

$P_1$ may be selected from an acrylate group, an epoxy group, and a vinyl group.

$P_1$ may be a group represented by one of the following Formulae 6-1 to 6-3:

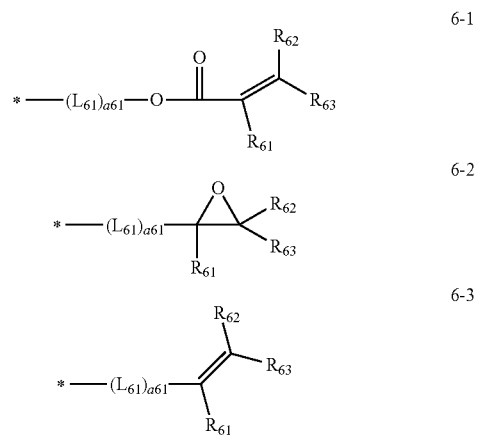

wherein, in Formulae 6-1 to 6-3, $L_{61}$ may be selected from a substituted or unsubstituted $C_1$-$C_{10}$ alkylene group and a substituted or unsubstituted $C_2$-$C_{10}$ alkenylene group; a61 may be selected from 0, 1, 2, 3, 4, and 5; $R_{61}$ to $R_{63}$ may each independently be selected from hydrogen, a substituted or unsubstituted $C_1$-$C_{10}$ alkyl group, and a substituted or unsubstituted $C_1$-$C_{10}$ alkoxy group; and * is a binding site with an adjacent atom.

The first compound may be represented by one of the following Formulae 1-1, 1-2, 2-1, and 2-2:

Formula 1-1

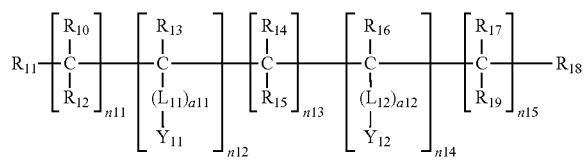

Formula 1-2

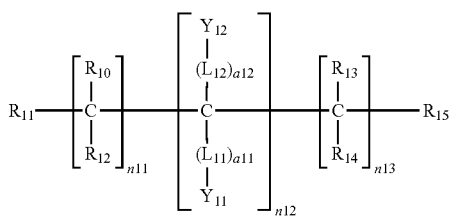

-continued

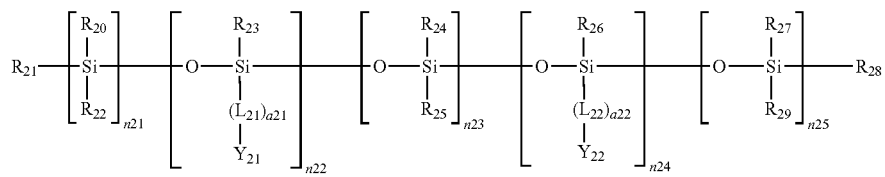
Formula 2-1

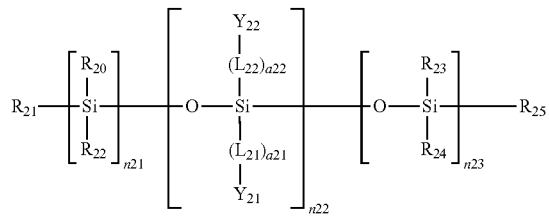
Formula 2-2 wherein, in Formulae 1-1, 1-2, 2-1, and 2-2, $Y_{11}$, $Y_{12}$, $Y_{21}$, and $Y_{22}$ may be each independently selected from a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group; $L_{11}$, $L_{12}$, $L_{21}$, and $L_{22}$ may be each independently selected from a substituted or unsubstituted $C_1$-$C_{10}$ alkylene group and a substituted or unsubstituted $C_2$-$C_{10}$ alkenylene group; a11, a12, a21, and a22 may be each independently selected from 0, 1, and 2; $R_{10}$ to $R_{19}$ and $R_{20}$ to $R_{29}$ may be each independently selected from hydrogen, deuterium, a substituted or unsubstituted $C_1$-$C_{10}$ alkyl group, a substituted or unsubstituted $C_3$-$C_{10}$ cycloalkyl group, and a polymerizable group $P_1$, wherein at least one of $R_{10}$ to $R_{19}$ is the polymerizable group $P_1$ and at least one of $R_{20}$ to $R_{29}$ is the polymerizable group $P_1$; n11 to n15 and n21 to n25 may be each independently selected from 0, 1, 2, 3, 4, and 5; a sum of n12 and n14 may be 1 or 2; and a sum of n22 and n24 may be 1 or 2.

The first compound may be represented by one of the following Formulae 1-11 to 1-18 and 2-11 to 2-18:

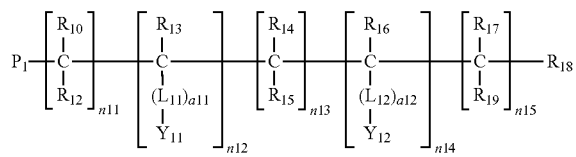
Formula 1-11

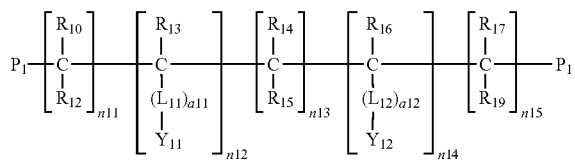
Formula 1-12

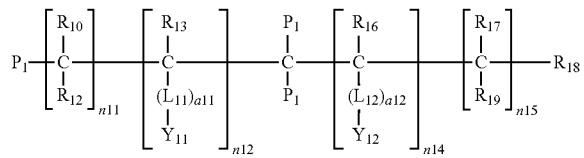
Formula 1-13

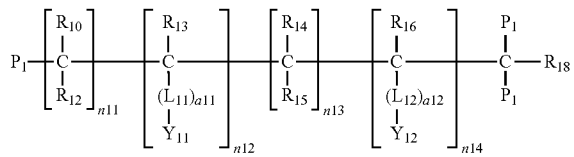
Formula 1-14

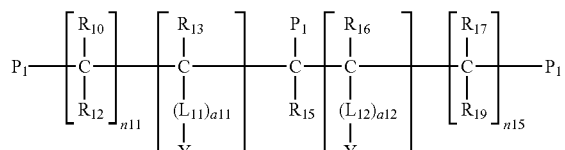
Formula 1-15

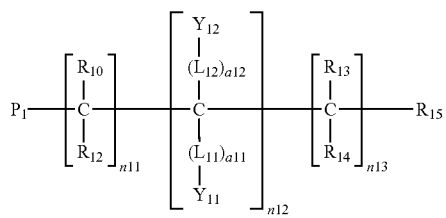
Formula 1-16

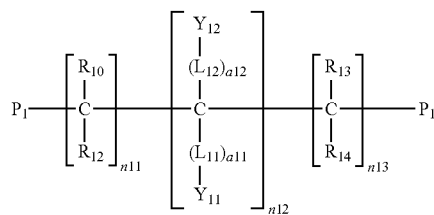
Formula 1-17

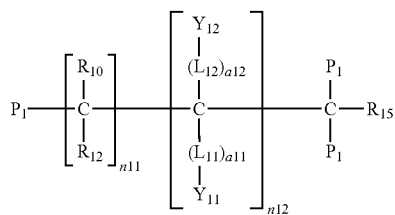
Formula 1-18

Formula 2-11

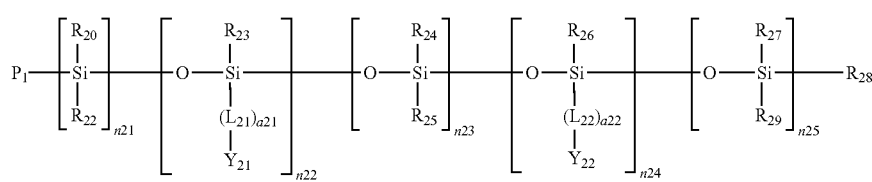

Formula 2-12

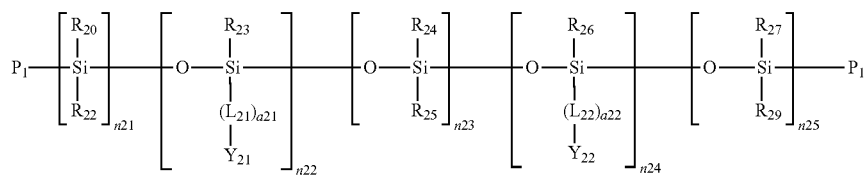

Formula 2-13

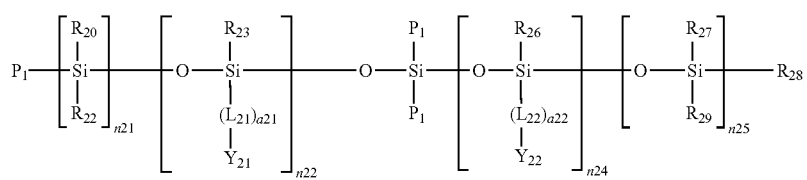

Formula 2-14

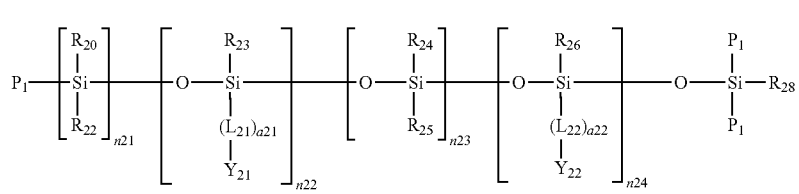

Formula 2-15

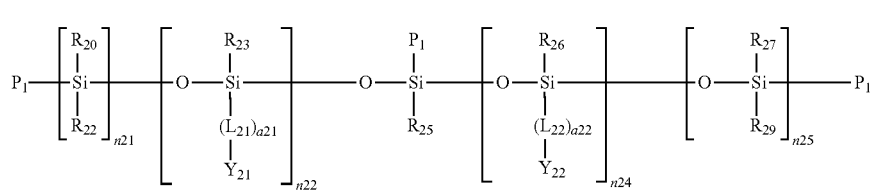

Formula 2-16

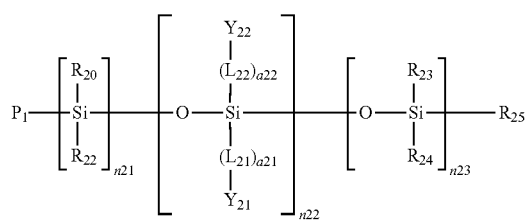

Formula 2-17

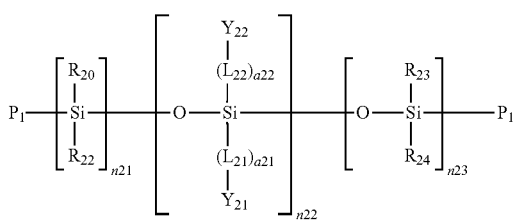

Formula 2-18

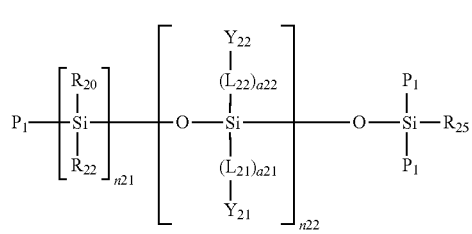

wherein, in Formulae 1-11 to 1-18 and 2-11 to 2-18, $Y_{11}$, $Y_{12}$, $Y_{21}$, and $Y_{22}$ may be each independently selected from a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group; $L_{11}$, $L_{12}$, $L_{21}$, and $L_{22}$ may be each independently selected from a substituted or unsubstituted $C_1$-$C_{10}$ alkylene group and a substituted or unsubstituted $C_2$-$C_{10}$ alkenylene group; a11, a12, a21, and a22 may be each independently selected from 0, 1, and 2; $R_{10}$ to $R_{19}$ and $R_{20}$ to $R_{29}$ may be each independently selected from hydrogen, deuterium, a substituted or unsubstituted $C_1$-$C_{10}$ alkyl group, and a substituted or unsubstituted $C_3$-$C_{10}$ cycloalkyl group; $P_1$ may be a group represented by one of the following Formulae 6-1 to 6-3;

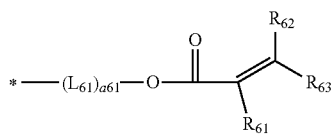

6-1

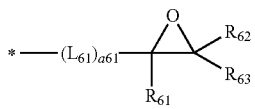

6-2

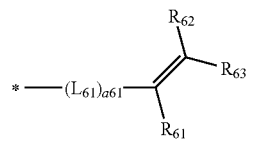

6-3

wherein, in Formulae 6-1 to 6-3, $L_{61}$ may be selected from a substituted or unsubstituted $C_1$-$C_{10}$ alkylene group and a substituted or unsubstituted $C_2$-$C_{10}$ alkenylene group; a61 may be selected from 0, 1, 2, and 3; $R_{61}$ to $R_{63}$ may be each independently selected from hydrogen, a substituted or unsubstituted $C_1$-$C_{10}$ alkyl group, and a substituted or unsubstituted $C_1$-$C_{10}$ alkoxy group; * is a binding site with an adjacent atom; n11 to n15 and n21 to n25 may be each independently selected from 0, 1, 2, 3, 4, and 5; a sum of n12 and n14 may be 1 or 2; and a sum of n22 and n24 may be 1 or 2.

The first compound may be one of the following Compounds 101 to 106:

101

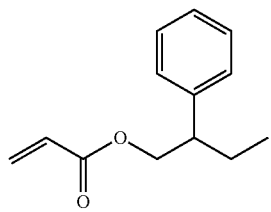

102

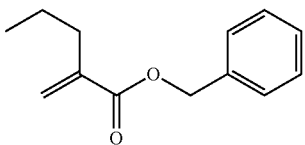

103

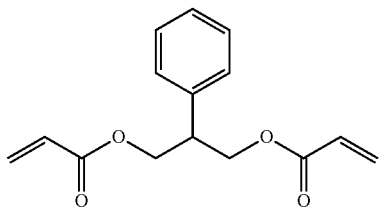

104

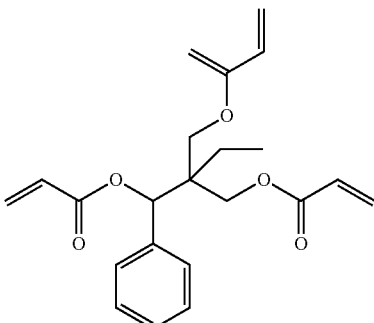

105

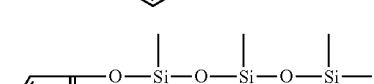

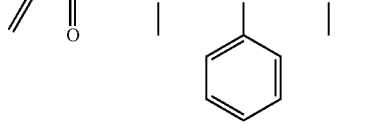

106

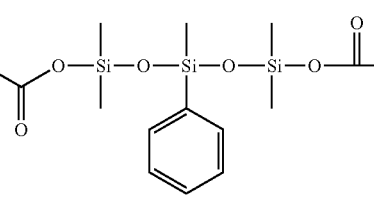

The composition may further include a second compound, wherein OP of the composition for fabricating an organic film may be equal to or greater than 2.8 and equal to or less than 4.8; OP being ($n_1 \cdot OP_1 + n_2 \cdot OP_2$); RP of the composition for fabricating an organic film may be equal to or greater than 0.01 and equal to or less than 0.46; RP being $n_1 \cdot RP_1$; $n_1$ is (number of moles of the first compound)/(number of moles of the first compound+number of moles of the second compound); $n_2$ is (number of moles of the second compound)/(number of moles of the first compound+number of moles of the second compound); $OP_1$ is (total number of atoms of the first compound)/{(number of carbon atoms of the first compound)−(number of oxygen atoms of the first compound)}; $RP_1$ is {(number of carbon atoms of the substituent Y)X n}/(number of carbon atoms of the first compound); and $OP_2$ is (total number of atoms of the second compound)/{(number of carbon atoms of the second compound)−(number of oxygen atoms of the second compound)}.

The composition may further include an initiator.

A viscosity of the composition may be about 1 cps to about 100 cps at 25° C.

The embodiments may be realized by providing an organic light-emitting display apparatus including a substrate; an organic light-emitting device on the substrate; and an encapsulation layer on the organic light-emitting device; wherein the encapsulation layer includes 1, 2, or 3 sealing units, each sealing unit including an organic film and an inorganic film that are sequentially stacked on the organic light-emitting device; the organic film includes a polymer prepared from a composition for fabricating an organic film that includes a first compound; the first compound including n substituents Y, n being selected from 1, 2, 3, and 4, and m polymerizable groups $P_1$, m being selected from 1, 2, 3, and 4; wherein $OP_1$ of the first compound is equal to or greater than 2.8 and equal to or less than 4.8; $RP_1$ of the first compound is equal to or greater than 0.01 and equal to or less than 0.46; $OP_1$ is (total number of atoms of the first compound)/{(number of carbon atoms of the first compound)−(number of oxygen atoms of the first compound)}; and $RP_1$ is {(number of carbon atoms of the substituent Y)X n}/(number of carbon atoms of the first compound).

The composition for fabricating an organic film may further include a second compound, OP of the composition for fabricating an organic film is equal to or greater than 2.8 and equal to or less than 4.8, OP being $(n_1 \cdot OP_1 + n_2 \cdot OP_2)$; RP of the composition for fabricating an organic film is equal to or greater than 0.01 and equal to or less than 0.46, RP being $n_1 \cdot RP_1$; $n_1$ is (number of moles of the first compound)/(number of moles of the first compound+number of moles of the second compound); $n_2$ is (number of moles of the second compound)/(number of moles of the first compound+number of moles of the second compound); $OP_1$ is (total number of atoms of the first compound)/{(number of carbon atoms of the first compound)−(number of oxygen atoms of the first compound)}; $RP_1$ is {(number of carbon atoms of the substituent Y)X n}/(number of carbon atoms of the first compound); and $OP_2$ is (total number of atoms of the second compound)/{(number of carbon atoms of the second compound)−(number of oxygen atoms of the second compound)}.

The inorganic film may include at least one selected from metal, metal nitride, metal oxide, metal oxynitride, silicon nitride, silicon oxide, and silicon oxynitride.

The encapsulation layer may further include a lower inorganic film interposed between the organic light-emitting device and the organic film.

The organic light-emitting display apparatus may further include at least one selected from a capping layer and a protective layer interposed between the organic light-emitting device and the encapsulation layer.

The embodiments may be realized by providing a method of manufacturing an organic light-emitting display apparatus, the method including forming an organic light-emitting device on a substrate; and forming an encapsulation layer that includes 1, 2, or 3 sealing units, each of the sealing units including an organic film and an inorganic film that are sequentially stacked on the organic light-emitting device, wherein forming the encapsulation layer includes forming the organic film by applying a composition for fabricating an organic film to a region where the organic film is to be formed and polymerizing the composition, the composition including a first compound; the first compound includes n substituents Y and m polymerizable groups $P_1$; n is selected from 1, 2, 3, and 4; m is selected from 1, 2, 3, and 4; $OP_1$ of the first compound is equal to or greater than 2.8 and equal to or less than 4.8; $OP_1$ being (total number of atoms of the first compound)/{(number of carbon atoms of the first compound)−(number of oxygen atoms of the first compound)}; and $RP_1$ of the first compound is equal to or greater than 0.01 and equal to or less than 0.46; $RP_1$ being {(number of carbon atoms of the substituent Y)X n}/(number of carbon atoms of the first compound).

Applying the composition may include performing flash evaporation or ink-jet printing.

Polymerizing the composition may include photocuring or thermal curing the composition.

Forming the encapsulation layer may include forming the inorganic film by chemical vapor deposition or reactive sputtering using oxygen gas or oxygen plasma.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
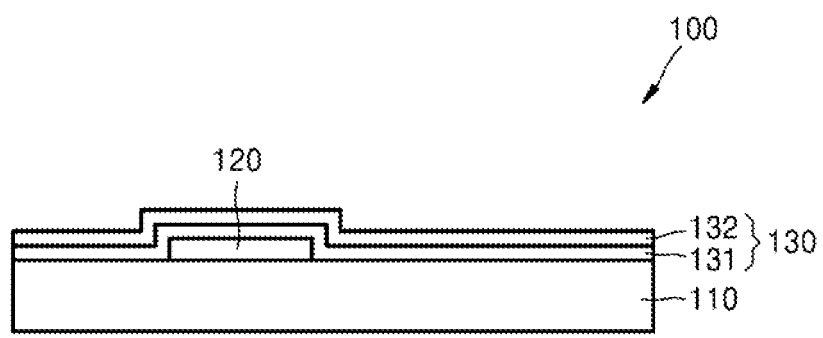
FIG. 1 illustrates a cross-sectional view of an organic light-emitting display apparatus according to an exemplary embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of" when preceding a list of elements, modify the entire list of elements and do not modify the individual elements of the list.

As used herein, the singular forms "a," "an" and "the" are intended to include the plural forms as well, unless the context clearly indicates otherwise.

It will be further understood that the terms "includes," "including," "comprises," and/or "comprising" used herein specify the presence of stated features or components, but do not preclude the presence or addition of one or more other features or components.

It will be understood that when a layer, region, or component is referred to as being "formed on," another layer, region, or component, it can be directly or indirectly formed on the other layer, region, or component. For example, intervening layers, regions, or components may be present.

FIG. 1 illustrates a cross-sectional view of an organic light-emitting display apparatus 100 according to an exemplary embodiment.

The organic light-emitting display apparatus 100 may include a substrate 110, an organic light-emitting device 120 on the substrate 110, and an encapsulation layer 130 on the organic light-emitting device 120.

The substrate 110, which may be a suitable substrate for organic light-emitting display apparatuses, may be, e.g., an inorganic material substrate or organic material substrate with excellent mechanical strength, thermal stability, transparency, surface smoothness, ease of handling, and waterproofness.

For example, the substrate 110 may be an inorganic material substrate formed of a transparent glass material including $SiO_2$ as a main component.

In an implementation, the substrate 110 may be, e.g., an insulating organic material substrate. The insulating organic material may be selected from, e.g., polyethersulphone (PES), polyacrylate (PAR), polyetherimide (PEI), polyethylene naphthalate (PEN), polyethylene terephthalate (PET), polyphenylene sulfide (PPS), polyallylate, polyimide, polycarbonate (PC), cellulose triacetate (TAC), and cellulose acetate propionate (CAP).

The organic light-emitting device 120 may be disposed on the substrate 110. The organic light-emitting device 120 may include a first electrode, an organic layer including an emission layer, and a second electrode.

The first electrode may be formed on the substrate 110 by depositing or sputtering a material used to form the first electrode. When the first electrode constitutes an anode, the material used to form the first electrode may be a high work function material so as to facilitate hole injection. The first electrode may be a reflective electrode or a transmissive electrode. The material used to form the first electrode may include at least one selected from indium tin oxide (ITO), indium zinc oxide (IZO), tin oxide (SnO$_2$), zinc oxide (ZnO), silver (Ag), magnesium (Mg), aluminum (Al), aluminum-lithium (Al—Li), calcium (Ca), magnesium-indium (Mg—In), and magnesium-silver (Mg—Ag).

The first electrode may have a single-layered or a multi-layered structure. For example, the first electrode may have a triple-layered structure of ITO/Ag/ITO, without being limited thereto.

The organic layer including the emission layer may be formed on the first electrode.

The organic layer may include a hole transport region interposed between the first electrode and the emission layer. The organic layer may include an electron transport region interposed between the emission layer and the second electrode.

The second electrode may be formed on the organic layer. The second electrode may be a cathode, which is an electron injecting electrode. A metal used to form the second electrode may be a metal having a low work function, or an alloy, an electrically conductive compound, or any mixture thereof. For example, the second electrode may be a transmissive electrode formed of lithium (Li), magnesium (Mg), aluminum (Al), an Al—Li alloy, calcium (Ca), an Mg—In alloy, or an Mg—Ag alloy in a thin film. In order to manufacture a top emission-type organic light-emitting device, a transmissive electrode formed of ITO or IZO may be used, and various modifications may be applied thereto.

The encapsulation layer 130 may be formed on the organic light-emitting device 120. The encapsulation layer 130 may be formed by, e.g., alternately stacking an organic film 131 and inorganic film 132. The encapsulation layer 130 may help reduce and/or prevent infiltration of external moisture and/or oxygen into the organic light-emitting device 120.

The encapsulation layer 130 may include, e.g., 1, 2, or 3 sealing units each including the organic film 131 and the inorganic film 132 alternately stacked on the organic light-emitting device 120. In an implementation, one sealing unit may be included (as illustrated in FIG. 1), or 2 or 3 sealing units may be included therein. When the encapsulation layer 130 includes one sealing unit, the organic light-emitting display apparatus 100 may include the organic light-emitting device 120, the organic film 131, and the inorganic film 132 sequentially stacked on the substrate 110.

The organic film 131 may planarize a structure under the organic film 131 and may cover particles generated while forming a structure under the organic film 131, and reliability of the encapsulation layer 130 may be improved.

The inorganic film 132 may substantially prevent infiltration of external moisture and/or oxygen.

The organic film 131 may be formed of a composition for fabricating an organic film. For example, the organic film 131 may include a polymer of or prepared from the composition for fabricating an organic film.

The composition for fabricating an organic film may include a first compound including n substituents Y and m polymerizable groups P$_1$, in which n may be selected from 1, 2, 3, and 4; m may be selected from 1, 2, 3, and 4. For example, the first compound may include 1, 2, 3, or 4 substituents Y and 1, 2, 3, or 4 polymerizable groups P$_1$.

OP$_1$ of the first compound may be equal to or greater than 2.8 and equal to or less than 4.8. For example, OP$_1$ is determined as follows: (total number of atoms of the first compound)/{(number of carbon atoms of the first compound)−(number of oxygen atoms of the first compound)}.

RP$_1$ of the first compound may be equal to or greater than 0.01 and equal to or less than 0.46. For example, RP$_1$ is determined as follows: {(number of carbon atoms of the substituent Y)X n}/(number of carbon atoms of the first compound).

The first compound may include a monomer, an oligomer, or a mixture thereof.

In the first compound, when n is 2 or greater, a plurality of Ys may be the same or different.

In the first compound, when m is 2 or greater, a plurality of P$_1$s may be the same or different.

For example, n may be 1 or 2.

In an implementation, Y may be selected from or include, e.g., a substituted or unsubstituted C$_6$-C$_{60}$ aryl group, a substituted or unsubstituted C$_6$-C$_{60}$ aryloxy group, and a substituted or unsubstituted C$_6$-C$_{60}$ arylthio group.

In an implementation, Y may be, e.g., a group represented by one of the following Formulae 5-1 to 5-9.

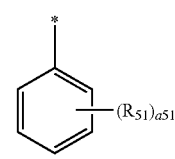

5-1

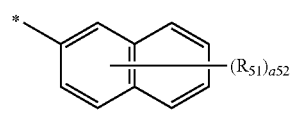

5-2

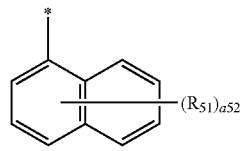

5-3

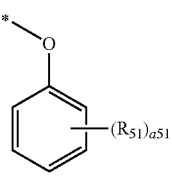

5-4

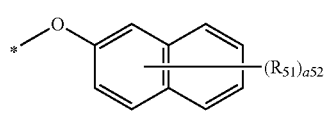

5-5

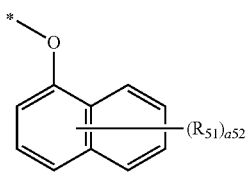

5-6

-continued

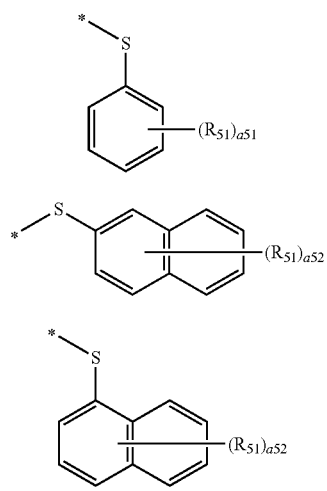

In Formulae 5-1 to 5-9, $R_{51}$ may be selected from, e.g., hydrogen, deuterium, —F, —Cl, —Br, —I, a cyano group, a nitro group, a $C_1$-$C_{10}$ alkyl group, a $C_1$-$C_{10}$ alkoxy group, and a $C_6$-$C_{30}$ aryl group;

a51 may be selected from, e.g., 1, 2, 3, 4, and 5;

a52 may be selected from, e.g., 1, 2, 3, 4, 5, 6, and 7; and

* is a binding site with an adjacent atom.

In an implementation, in Formulae 5-1 to 5-9, $R_{51}$ may be selected from, e.g., hydrogen, a methyl group, an ethyl group, a tert-butyl group, a methoxy group, an ethoxy group, a tert-butoxy group, a phenyl group, and a naphthyl group;

In an implementation, Y may be, e.g., a group represented by one of the following Formulae 5-11 to 5-28.

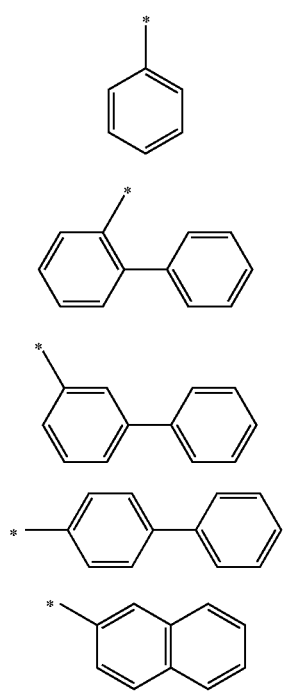

-continued

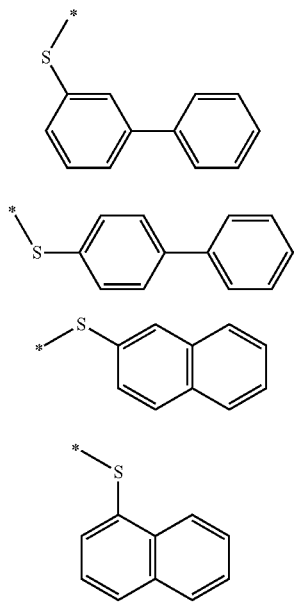

5-25

5-26

5-27

5-28

In Formulae 5-11 to 5-28, * is a binding site with an adjacent atom.

In an implementation, m may be selected from, e.g., 1, 2, and 3.

In an implementation, $P_1$ may be selected from, e.g., an acrylate group, an epoxy group, and a vinyl group.

In an implementation, $P_1$ may be, e.g., a group represented by one of the following Formulae 6-1 to 6-3.

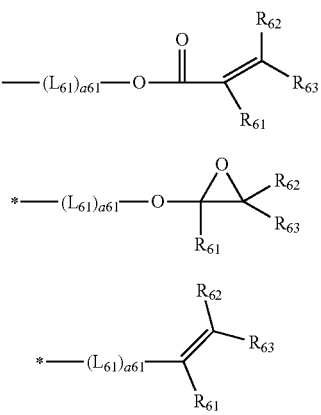

6-1

6-2

6-3

In Formulae 6-1 to 6-3, $L_{61}$ may be selected from or include, e.g., a substituted or unsubstituted $C_1$-$C_{10}$ alkylene group and a substituted or unsubstituted $C_2$-$C_{10}$ alkenylene group;

a61 may be selected from, e.g., 0, 1, 2, 3, 4, and 5;

$R_{61}$ to $R_{63}$ may each independently be selected from or include, e.g., hydrogen, a substituted or unsubstituted $C_1$-$C_{10}$ alkyl group, and a substituted or unsubstituted $C_1$-$C_{10}$ alkoxy group; and

* is a binding site with an adjacent atom.

In an implementation, in Formulae 6-1 to 6-3, $L_{61}$ may be selected from, e.g., a methylene group and an ethylene group; a61 may be selected from, e.g., 0, 1, 2, and 3; and/or $R_{61}$ to $R_{63}$ may each independently be selected from, e.g., hydrogen, a methyl group, an ethyl group, an n-propyl group, and a methoxy group.

In an implementation, $P_1$ may be, e.g., a group represented by one of the following Formulae 6-1A, 6-1B, 6-1C, and 6-1D.

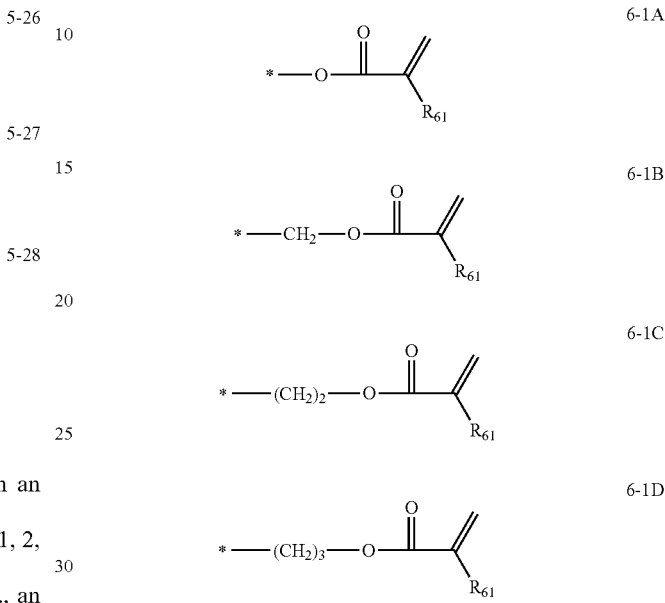

6-1A 6-1B 6-1C 6-1D

In Formulae 6-1A, 6-1B, 6-1C, and 6-1D, $R_{61}$ may be selected from, e.g., hydrogen, a methyl group, an ethyl group, and an n-propyl group; and

* is a binding site with an adjacent atom.

In an implementation, $P_1$ may be, e.g., a group represented by one of the following Formulae 6-11 to 6-18.

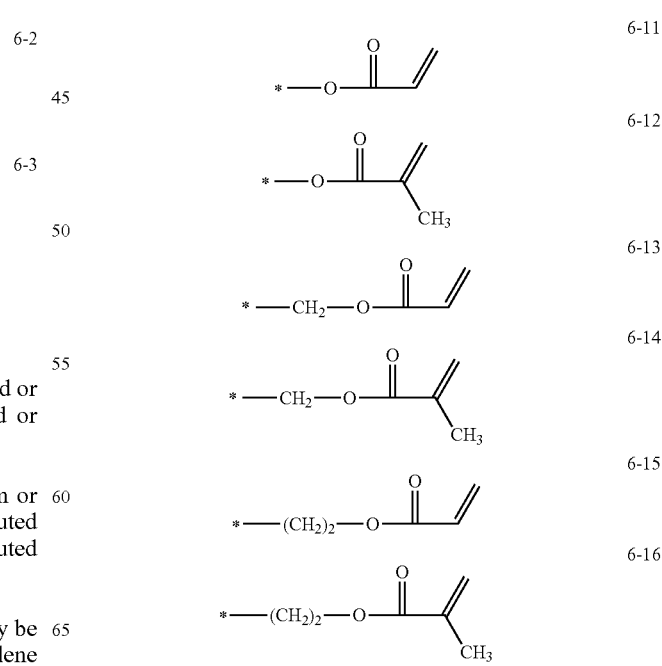

6-11

6-12

6-13

6-14

6-15

6-16

-continued

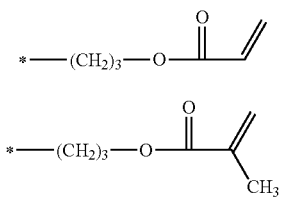
6-17

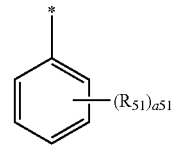
6-18

In Formulae 6-11 to 6-18, * is a binding site with an adjacent atom.

In an implementation, the first compound may be, e.g., represented by one of the following Formulae 1-1, 1-2, 2-1, and 2-2.

Formula 1-1
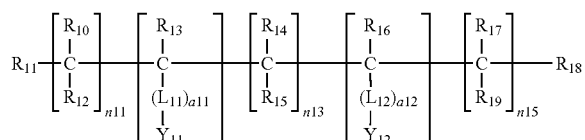

Formula 1-2
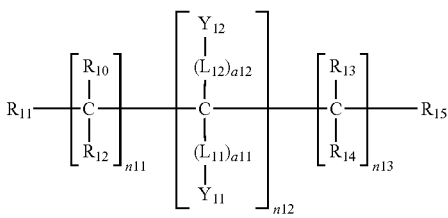

Formula 2-1
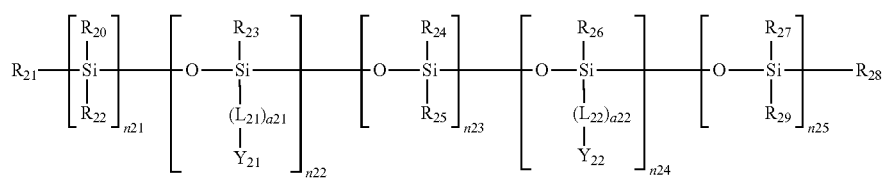

Formula 2-2
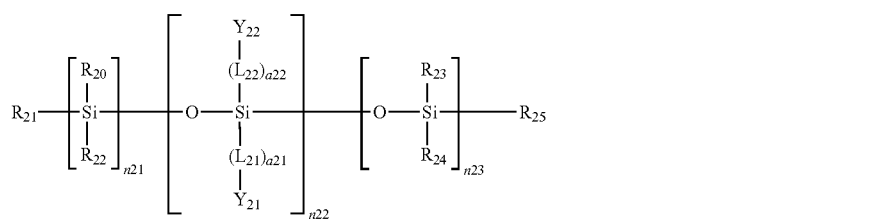

In Formulae 1-1, 1-2, 2-1, and 2-2, $Y_{11}$, $Y_{12}$, $Y_{21}$, and $Y_{22}$ may each independently be selected from or include, e.g., a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group;

$L_{11}$, $L_{12}$, $L_{21}$, and $L_{22}$ may each independently be selected from or include, e.g., a substituted or unsubstituted $C_1$-$C_{10}$ alkylene group and a substituted or unsubstituted $C_2$-$C_{10}$ alkenylene group;

a11, a12, a21, and a22 may each independently be selected from 0, 1, and 2;

$R_{10}$ to $R_{19}$ and $R_{20}$ to $R_{29}$ may each independently be selected from or include, e.g., hydrogen, deuterium, a substituted or unsubstituted $C_1$-$C_{10}$ alkyl group, a substituted or unsubstituted $C_3$-$C_{10}$ cycloalkyl group, and a polymerizable group $P_1$. In an implementation, at least one of $R_{10}$ to $R_{19}$ may be the polymerizable group $P_1$ and at least one of $R_{20}$ to $R_{29}$ is the polymerizable group $P_1$.

n11 to n15 and n21 to n25 may each independently be selected from 0, 1, 2, 3, 4, and 5;

a sum of n12 and n14 may be 1 or 2; and a sum of n22 and n24 may be 1 or 2.

In an implementation, in Formulae 1-1, 1-2, 2-1, and 2-2, $Y_{11}$, $Y_{12}$, $Y_{21}$, and $Y_{22}$ may each independently be, e.g., a group represented by one of the following Formulae 5-1 to 5-9.

5-1
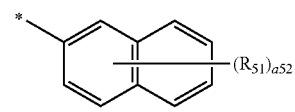

-continued 5-2
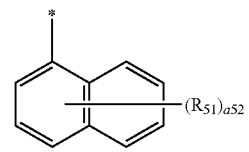

5-3

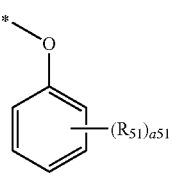

5-4

-continued

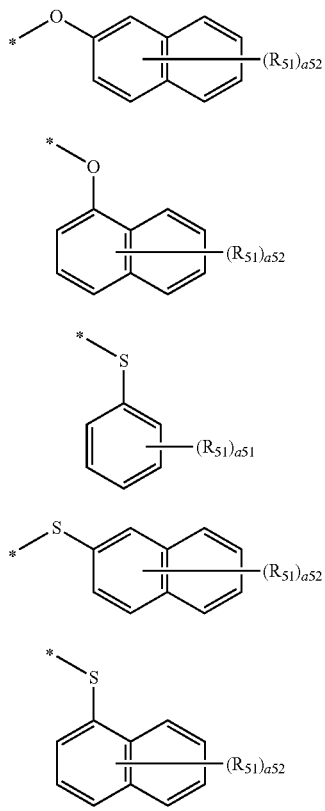

In Formulae 5-1 to 5-9, $R_{51}$ may be selected from, e.g., hydrogen, deuterium, —F, —Cl, —Br, —I, a cyano group, a nitro group, a $C_1$-$C_{10}$ alkyl group, a $C_1$-$C_{10}$ alkoxy group, and a $C_6$-$C_{30}$ aryl group;

a51 may be selected from 1, 2, 3, 4, and 5;

a52 may be selected from 1, 2, 3, 4, 5, 6, and 7; and

* is a binding site with an adjacent atom.

In an implementation, in Formulae 1-1, 1-2, 2-1, and 2-2, $L_{11}$, $L_{12}$, $L_{21}$, and $L_{22}$ may each independently be selected from, e.g., a methylene group, an ethylene group, and a propylene group.

In an implementation, in Formulae 1-1, 1-2, 2-1, and 2-2, $R_{10}$ to $R_{19}$ and $R_{20}$ to $R_{29}$ may each independently be selected from, e.g., hydrogen, deuterium, a methyl group, an ethyl group, an n-propyl group, an iso-propyl group, an n-butyl group, an iso-butyl group, a sec-butyl group, a tert-butyl group, and a polymerizable group $P_1$. In an implementation, at least one of $R_{10}$ to $R_{19}$ may be the polymerizable group $P_1$ and at least one of $R_{20}$ to $R_{29}$ may be the polymerizable group $P_1$.

In an implementation, the first compound may be, e.g., represented by one of the following Formulae 1-11 to 1-18 and 2-11 to 2-18.

Formula 1-11

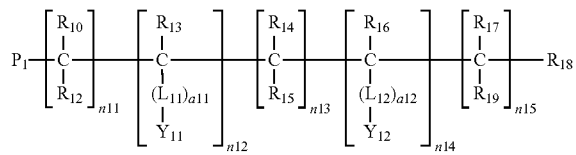

Formula 1-12

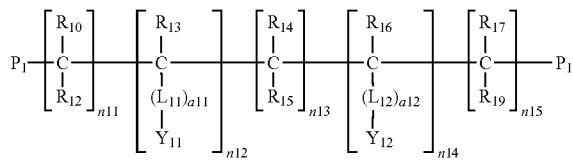

Formula 1-13

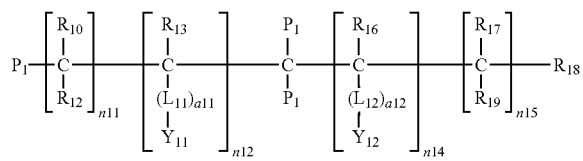

Formula 1-14

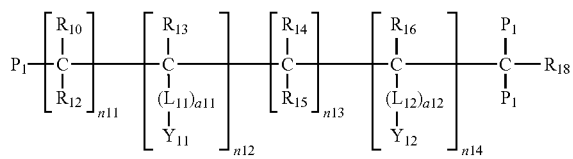

Formula 1-15

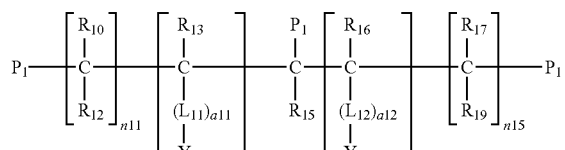

Formula 1-16

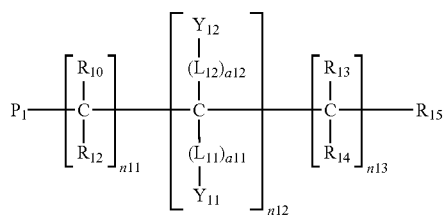

-continued
Formula 1-17
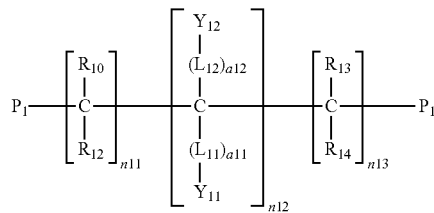
Formula 1-18
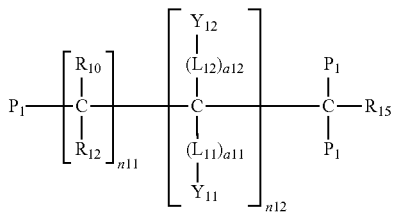
Formula 2-11
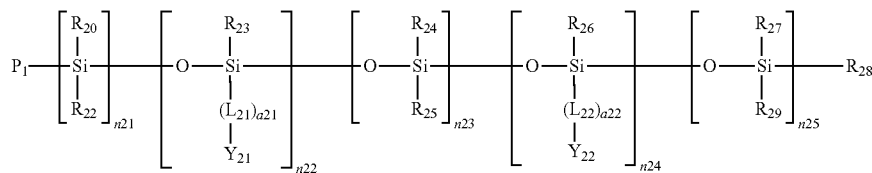
Formula 2-12
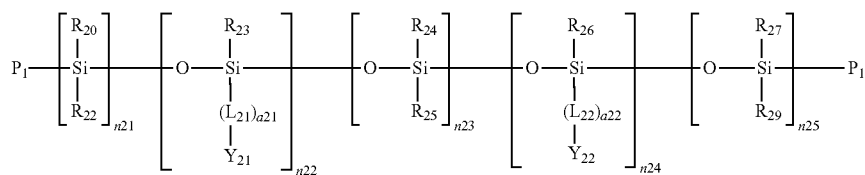
Formula 2-13
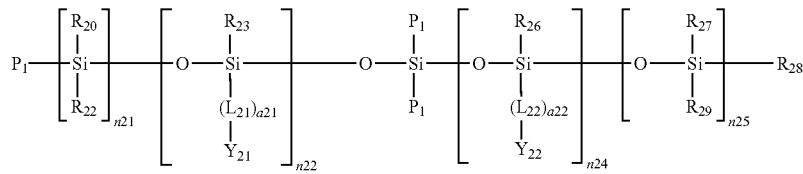
Formula 2-14
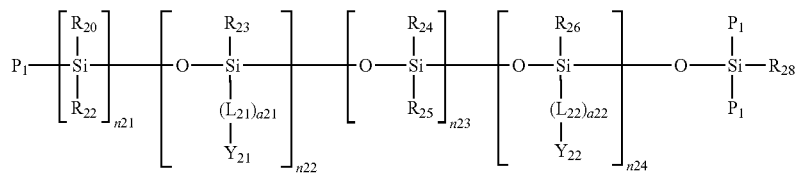
Formula 2-15
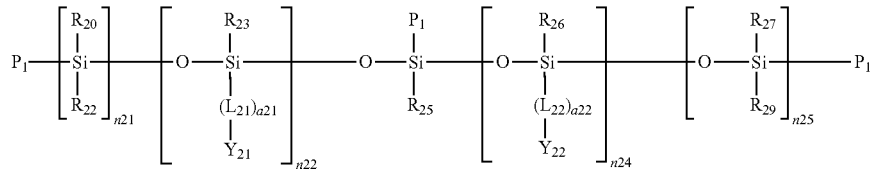
Formula 2-16
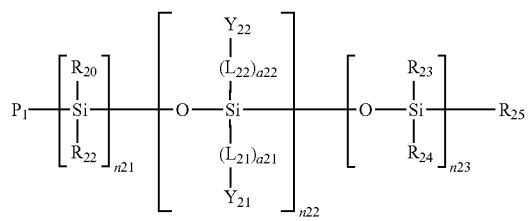
Formula 2-17
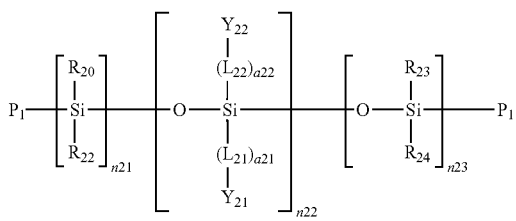
Formula 2-18
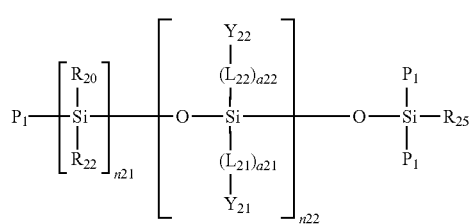

In Formulae 1-11 to 1-18 and 2-11 to 2-18, $Y_{11}$, $Y_{12}$, $Y_{21}$, and $Y_{22}$ may each independently be selected from or include, e.g., a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group;

$L_{11}$, $L_{12}$, $L_{21}$, and $L_{22}$ may each independently be selected from or include, e.g., a substituted or unsubstituted $C_1$-$C_{10}$ alkylene group and a substituted or unsubstituted $C_2$-$C_{10}$ alkenylene group;

a11, a12, a21, and a22 may each independently be selected from 0, 1, and 2;

$R_{10}$ to $R_{19}$ and $R_{20}$ to $R_{29}$ may each independently be selected from or include, e.g., hydrogen, deuterium, a substituted or unsubstituted $C_1$-$C_{10}$ alkyl group, and a substituted or unsubstituted $C_3$-$C_{10}$ cycloalkyl group; and $P_1$ may be, e.g., a group represented by one of the following Formulae 6-1 to 6-3.

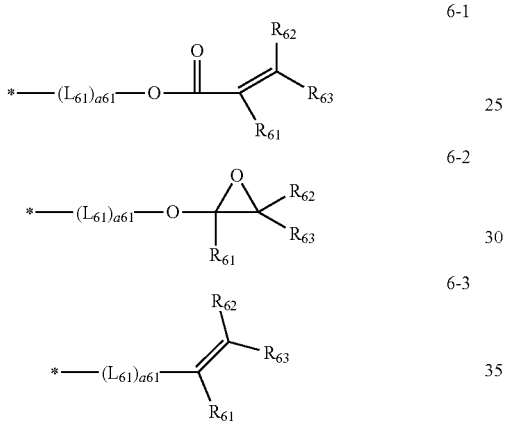

In Formulae 6-1 to 6-3, $L_{61}$ may be selected from or include, e.g., a substituted or unsubstituted $C_1$-$C_{10}$ alkylene group and a substituted or unsubstituted $C_2$-$C_{10}$ alkenylene group;

a61 may be selected from 0, 1, 2, and 3;

$R_{61}$ to $R_{63}$ may each independently be selected from or include, e.g., hydrogen, a substituted or unsubstituted $C_1$-$C_{10}$ alkyl group, and a substituted or unsubstituted $C_1$-$C_{10}$ alkoxy group;

* is a binding site with an adjacent atom;

n11 to n15 and n21 to n25 may each independently be selected from 0, 1, 2, 3, 4, and 5;

a sum of n12 and n14 may be 1 or 2; and a sum of n22 and n24 may be 1 or 2.

In an implementation, the first compound may be, e.g., one of the following Compounds 101 to 106.

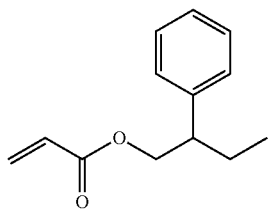

101

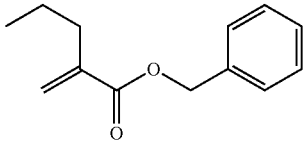

102

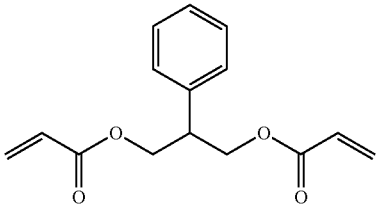

103

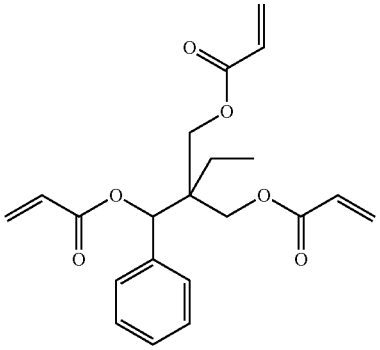

104

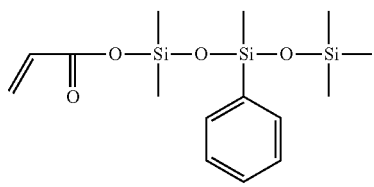

105

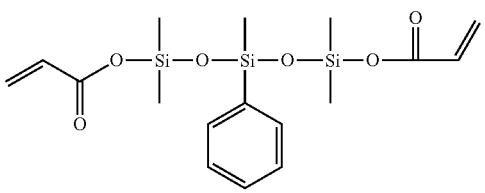

106

The first compound may have high durability against plasma. Thus, when the inorganic film 132 is formed by PECVD or sputtering, which may degrade the organic film 131, after forming the organic film 131 by using the composition for fabricating an organic film including the first compound, degradation of the organic film 131 may be inhibited. In addition, the first compound may provide physical properties such as viscosity that is suitable for a process of forming the organic film 131, and speed and economic efficiency of the process of forming the organic film 131 may be improved.

The first compound may be included in the composition in an amount of about 5% by weight to about 80% by weight, e.g., about 30% by weight to about 40% by weight, based on the weight of the composition for fabricating an organic film. When the amount of the first compound is within the ranges described above, not only reliability but also manufacturing efficiency of the organic light-emitting display apparatus may be improved.

In an implementation, the composition for fabricating an organic film may further include a second compound.

OP of the composition for fabricating an organic film may be, e.g., equal to or greater than 2.8 and equal to or less than 4.8 or about 2.8 to about 4.8. OP is determined as follows $(n_1 \cdot OP_1 + n_2 \cdot OP_2)$.

RP of the composition for fabricating an organic film may be, e.g., equal to or greater than 0.01 and equal to or less than 0.46 or about 0.01 to about 0.46. RP is determined as follows $n_1 \cdot RP_1$;

$n_1$ is (number of moles of the first compound)/(number of moles of the first compound+number of moles of the second compound);

$n_2$ is (number of moles of the second compound)/(number of moles of the first compound+number of moles of the second compound);

$OP_1$ is (total number of atoms of the first compound)/{(number of carbon atoms of the first compound)−(number of oxygen atoms of the first compound)};

$RP_1$ is {(number of carbon atoms of the substituent Y)X n}/(number of carbon atoms of the first compound); and $OP_2$ is (total number of atoms of the second compound)/{(number of carbon atoms of the second compound)−(number of oxygen atoms of the second compound)}, without being limited thereto.

In an implementation, the second compound may be represented by one of the following Formula 3 or Formula 4.

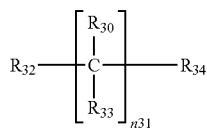

Formula 3

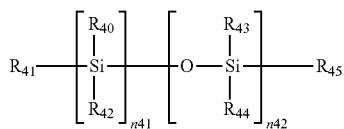

Formula 4

In Formulae 3 and 4, $R_{30}$ to $R_{34}$ and $R_{40}$ to $R_{45}$ may each independently be selected from or include, e.g., hydrogen, deuterium, a substituted or unsubstituted $C_1$-$C_{10}$ alkyl group, a substituted or unsubstituted $C_3$-$C_{10}$ cycloalkyl group, and a polymerizable group $P_2$. In an implementation, at least one of $R_{30}$ to $R_{34}$ may be the polymerizable group $P_2$ and at least one of $R_{40}$ to $R_{45}$ may be the polymerizable group $P_2$.

$P_2$ may be selected from, e.g., an acrylate group, an epoxy group, and a vinyl group; and n31, n41, and n42 may each independently be selected from integers from 0 to 20.

In an implementation, in Formulae 3 and 4, $R_{30}$ to $R_{34}$ and $R_{40}$ to $R_{45}$ may each independently be selected from, e.g., hydrogen, deuterium, a methyl group, an ethyl group, an n-propyl group, an iso-propyl group, an n-butyl group, an iso-butyl group, a sec-butyl group, a tert-butyl group, and a polymerizable group $P_2$. In an implementation, at least one of $R_{30}$ to $R_{34}$ may be the polymerizable group $P_2$ and at least one of $R_{40}$ to $R_{45}$ may be the polymerizable group $P_2$.

$P_2$ may be, e.g., a group represented by one of the following Formulae 6-1 to 6-3.

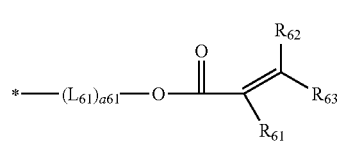

6-1

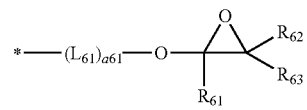

6-2

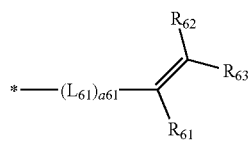

6-3

In Formulae 6-1 to 6-3, $L_{61}$ may be selected from or include, e.g., a substituted or unsubstituted $C_1$-$C_{10}$ alkylene group and a substituted or unsubstituted $C_2$-$C_{10}$ alkenylene group;

a61 may be selected from 0, 1, 2, 3, 4, and 5;

$R_{61}$ to $R_{63}$ may each independently be selected from or include, e.g., hydrogen, a substituted or unsubstituted $C_1$-$C_{10}$ alkyl group, and a substituted or unsubstituted $C_1$-$C_{10}$ alkoxy group;

* is a binding site with an adjacent atom; and n31, n41, and n42 may each independently be selected from integers from 0 to 15.

In an implementation, the second compound may be, e.g., represented by one of the following Formulae 3-1 to 3-3, 4-1, and 4-2.

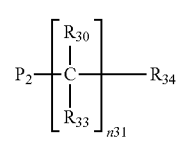

Formula 3-1

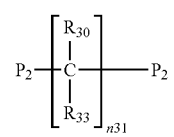

Formula 3-2

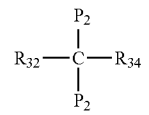

Formula 3-3

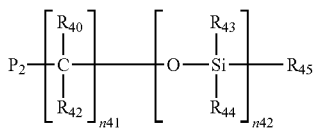

Formula 4-1

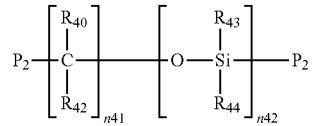

Formula 4-2

In Formulae 3-1 to 3-3, 4-1, and 4-2, $R_{30}$ to $R_{34}$ and $R_{40}$ to $R_{45}$ may each independently be selected from, e.g., hydrogen, deuterium, a methyl group, an ethyl group, an n-propyl group, an iso-propyl group, an n-butyl group, an iso-butyl group, a sec-butyl group, a tert-butyl group, and a polymerizable group $P_2$. In an implementation, at least one of $R_{30}$ to $R_{34}$ may be the polymerizable group $P_2$ and at least one of $R_{40}$ to $R_{45}$ may be the polymerizable group $P_2$.

$P_2$ may be, e.g., a group represented by one of the following Formulae 6-1 to 6-3.

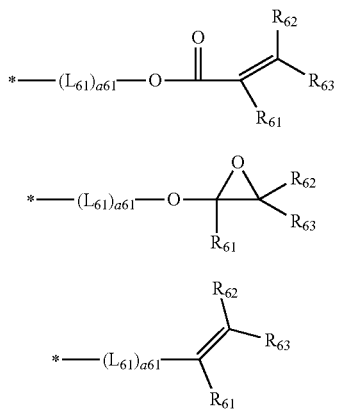

In Formulae 6-1 to 6-3, $L_{61}$ may be selected from or include, e.g., a substituted or unsubstituted $C_1$-$C_{10}$ alkylene group and a substituted or unsubstituted $C_2$-$C_{10}$ alkenylene group;

a61 may be selected from 0, 1, 2, and 3;

$R_{61}$ to $R_{63}$ may each independently be selected from or include, e.g., hydrogen, a substituted or unsubstituted $C_1$-$C_{10}$ alkyl group, and a substituted or unsubstituted $C_1$-$C_{10}$ alkoxy group;

* is a binding site with an adjacent atom; and n31, n41, and n42 may each independently be selected from integers from 0 to 15.

In an implementation, the second compound may be, e.g., one of the following Compounds 201 to 203:

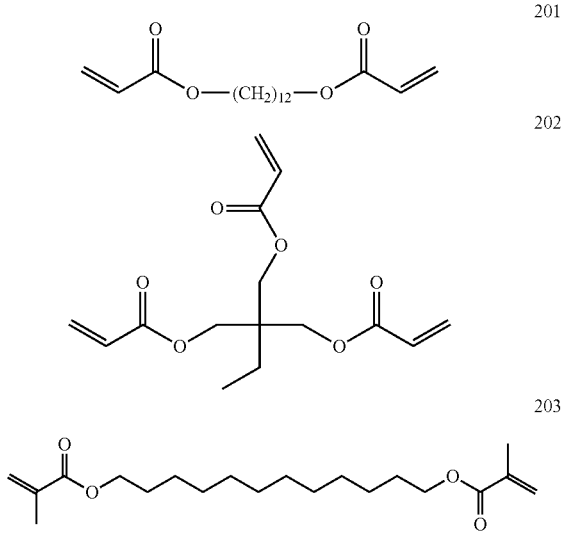

The second compound may serve as a starting material of polymerization together with the first compound contributing to formation of a polymer of the composition for fabricating an organic film.

When the composition for fabricating an organic film includes the second compound as described above, the second compound may be included in an amount of about 20% by weight to about 95% by weight, e.g., about 60% by weight to about 70% by weight, based on the weight of the composition for fabricating an organic film. When the amount of the second compound is within the ranges described above, a rate of polymerization of the composition for fabricating an organic film may be improved and the transparency of the organic film 131 may be increased.

In an implementation, the composition for fabricating an organic film may further include an initiator. The initiator may be a suitable material to initiate polymerization of the composition for fabricating an organic film.

In an implementation, the initiator may be a thermal initiator, such as an organic peroxide-based compound and an azo-based compound, or a photo initiator such as a benzophenone-based compound, an oxime-based compound, and a phosphine oxide-based compound.

Examples of the organic peroxide-based compound may include benzoyl peroxide, t-butyl peroxybenzoate, o-methyl benzoyl peroxide, p-methyl benzoyl peroxide, di-t-butyl peroxide, dicumyl peroxide, 1,1-bis(t-butylperoxy)-3,3,5-trimethyl cyclohexane, 1,1-di(t-butylperoxy)cyclohexane, 2,5-dimethyl-2,5-di(t-butylperoxy)hexane, 2,5-di(t-butylperoxy)-2,5-dimethyl-hexyne, 1,6-bis(p-toluoyl peroxy carbonyloxy)hexane, and di(4-methylbenzoylperoxy) hexamethylene biscarbonate.

Examples of the azo-based compound may include 2'-azobis(4-methoxy-2,4-dimethyl valeronitrile), 2,2'-azobis(2,4-dimethyl) valeronitrile, azobis isobutyronitrile, and 2,2'-azobis(2-methyl butyronitrile).

Examples of the benzophenone-based compound may include 2-hydroxy-2-methyl-1-phenyl-1-propanone, 2-hydroxy-1-[4-(2-hydroxyethoxy)phenyl]-2-methyl-1-propanone, alpha-dimethoxy-alpha-phenylacetophenone, 2-benzyl-2-(dimethylamino)-1-[4-(4-morpholinyl)phenyl]-1-butanone, and 2-methyl-1-[4-(methylthio)phenyl]-2-(4-morpholinyl)-1-propanone.

Examples of the oxime-based compound may include (hydroxyimino)cyclohexane, 1-[4-(phenylthio)phenyl]-octane-1,2-dione-2-(0-benzoyloxime), 1-[9-ethyl-6-(2-methylbenzoyl)-9H-carbazol-3-yl]-ethanone-1-(0-acetyloxime), trichloromethyl-triazine derivatives, 4-(4-methoxystyryl)-2,6-trichloromethyl-1,3,5-triazine, 4-(4-methoxyphenyl)-2,6-trichloromethyl-1,3,5-triazine, and ∝-aminoketone (1-(4-morpholinophenyl)-2-dimethylamino-2-benzyl-butan-1-one).

Examples of the phosphine oxide-based compound may include diphenyl(2,4,6-trimethylbenzoyl)-phosphine oxide (TPO) and phenyl bis(2,4,6-trimethyl benzoyl)phosphine oxide (BAPO).

An amount of the initiator may be selected within a suitable range. In an implementation, the initiator may be included in an amount of, e.g., about 0.01% by weight to about 10% by weight, based on the weight of the composition for fabricating an organic film.

In an implementation, the viscosity of the composition for fabricating an organic film may be in a range of about 1 cps to about 100 cps at 25° C., e.g., about 10 cps to about 50 cps at 25° C. When the viscosity of the composition for fabricating an organic film is within the ranges described above, ease of manufacturing the composition for fabricating an organic film may be improved and the polymer of the composition for fabricating an organic film may have excellent planarization properties.

In an implementation, a thickness of the organic film 131 may be in a range of about 0.1 µm to about 50 µm, e.g., about 1 µm to about 10 µm. When the thickness of the organic film 131 is within the ranges described above, planarization of the structure under the organic film 131 may be efficiently performed.

The composition for fabricating an organic film may be applied to a region where the organic film will be formed using suitable methods such as flash evaporation, spin coating, dip coating, and ink-jet printing, without being limited thereto. For example, the composition for fabricating an organic film may be applied to the region where the organic film will be formed by flash evaporation or ink-jet printing.

Then, the composition for fabricating an organic film applied to the region may be polymerized by, e.g., photo-curing or thermal curing. For example, the composition for fabricating an organic film may be polymerized by known methods such as UV curing, infrared curing, and laser curing.

The inorganic film 132 may include an inorganic material suitable for forming encapsulation layers. For example, the inorganic film 132 may include at least one selected from metal, metal nitride, metal oxide, metal oxynitride, silicon nitride, silicon oxide, and silicon oxynitride. For example, the inorganic film 132 may include at least one selected from aluminum oxide, silicon oxide, silicon nitride, and silicon oxynitride.

A thickness of the inorganic film 132 may be in a range of about 100 Å to about 15,000 Å, e.g., about 500 Å to about 3,000 Å. When the thickness of the inorganic film 132 is within the ranges described above, the encapsulation layer 130 may efficiently block moisture and/or oxygen.

The inorganic film 132 may be formed by, e.g., sputtering, reactive sputtering, chemical vapor deposition (CVD), plasma-enhanced chemical vapor deposition (PECVD), evaporation, electron cyclotron resonance PECVD, physical vapor deposition, atomic layer deposition (ALD), and the like. For example, the inorganic film 132 may be formed by reactive sputtering by using oxygen gas or oxygen plasma or CVD.

In an implementation, the encapsulation layer 130 may further include a lower inorganic film interposed between the organic light-emitting device 120 and the organic film 131. The lower inorganic film may enhance the ability of the encapsulation layer 130 to block moisture and/or oxygen. The lower inorganic film is as described above with reference to the inorganic film 132.

In an implementation, a thickness of the encapsulation layer 130 may be in a range of about 0.1 µm to about 1,000 µm, e.g., about 1 µm to about 10 µm. When the thickness of the encapsulation layer 130 is within the ranges described above, the encapsulation layer 130 may efficiently block infiltration of moisture and/or oxygen into the organic light-emitting device 120 and may have flexibility.

In an implementation, at least one of a capping layer and a protective layer may further be interposed between the organic light-emitting device 120 and the encapsulation layer 130.

The capping layer may be formed on the organic light-emitting device 120. The capping layer may induce constructive interference of light emitted from the organic light-emitting device 120, thereby increasing light coupling efficiency. The capping layer may be formed of a material having a relatively high refractive index, e.g., an organic metal complex such as Alq$_3$, silicon oxide, and silicon nitride.

The protective layer may be formed on the capping layer or the organic light-emitting device 120. The protective layer may help prevent damage of the capping layer or damage of the organic light-emitting device 120 caused during the formation of the encapsulation layer 130. For example, the protective layer may include lithium fluoride, silicon oxide, silicon nitride, and the like.

In an implementation, an upper inorganic film may further be formed on the encapsulation layer 130. The upper inorganic film may enhance adhesive force between a film to be attached to the organic light-emitting display apparatus 100 and the organic light-emitting display apparatus 100. The upper inorganic film is as described above with reference to the inorganic film 132.

Figure 2:
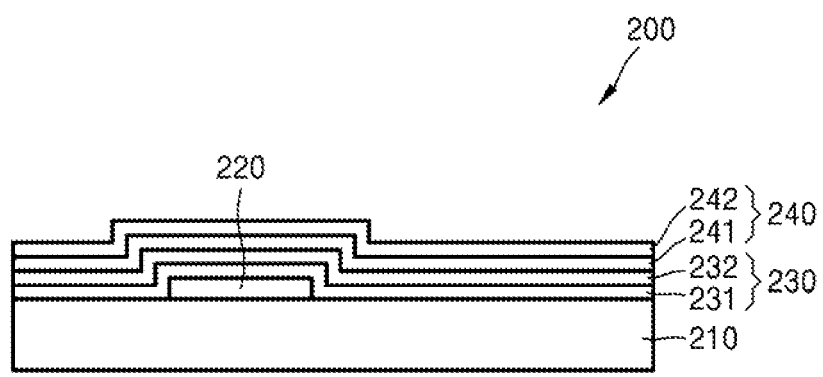
FIG. 2 illustrates a cross-sectional view of an organic light-emitting display apparatus according to another exemplary embodiment.

FIG. 2 illustrates a cross-sectional view of an organic light-emitting display apparatus 200 according to another exemplary embodiment.

The organic light-emitting display apparatus 200 may include a substrate 210, an organic light-emitting device 200 on the substrate 210, and an encapsulation layer on the organic light-emitting device 220.

The encapsulation layer may include a first sealing unit 230 and a second sealing unit 240.

The first sealing unit 230 may include a first organic film 231 and a first inorganic film 232 that are sequentially stacked on the organic light-emitting device 220.

The second sealing unit 240 may include a second organic film 241 and a second inorganic film 242 that are sequentially stacked on the first sealing unit 230.

The first organic film 231 and the second organic film 241 may be as described above with reference to the organic film 131. A thickness of the first organic film 231 may be the same as or different from that of the second organic film 241. Materials used to form the first organic film 231 and the second organic film 241 may be the same or different.

The first inorganic film 232 and the second inorganic film 242 are as described above with reference to the inorganic film 132. A thickness of the first inorganic film 232 may be the same as or different from that of the second inorganic film 242. Materials used to form the first inorganic film 232 and the second inorganic film 242 may be the same or different.

Hereinafter, a method of manufacturing the organic light-emitting display apparatus 100 will be described.

An organic light-emitting device 120 may be formed on a substrate 110. The organic light-emitting device 120 may be formed using a suitable method.

In an implementation, a lower inorganic film may be formed on the organic light-emitting device 120 to cover the organic light-emitting device 120. The lower inorganic film is as described above.

A composition for fabricating an organic film may be applied to the lower inorganic film at a region where an organic film will be formed and polymerized to form an organic film 131. The composition for fabricating an organic film is as described above and the organic film 131 is as described above.

An inorganic film 132 may be formed on the organic film 131. The inorganic film 132 is as described above.

An organic light-emitting display apparatus including one or two sealing units is described above. When the encapsulation layer includes two or more encapsulation layers, another layer, e.g., an organic film and an inorganic film contained in an encapsulation layer of a conventional organic light-emitting display apparatus, may further be interposed between the encapsulation layers, and various other modifications may also be applied thereto.

Hereinafter, an organic light-emitting device according to one or more embodiments will be described in detail with reference to the following synthesis examples and examples. These synthesis examples and examples are not intended to limit the purpose and scope of the one or more embodiments.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example 1

A composition for fabricating an organic film was prepared by mixing compounds listed in Table 1 below in a weight ratio described in Table 1.

TABLE 1

|  | First compound | Second compound | Initiator |
| --- | --- | --- | --- |
| Example 1 | Compound 102 (33.98% by weight) | Compound 203 (63.11% by weight) | TPO (2.91% by weight) |

Viscosity of the composition for fabricating an organic film was measured using a Brookfield DE-II+Pro viscometer at 25° C., and the results are shown in Table 2 below.

TABLE 2

|  | Viscosity (cps) |
| --- | --- |
| Example 1 | 20 |

Comparative Examples 1 and 2

A composition for fabricating an organic film was prepared by mixing compounds listed in Table 3 below in a weight ratio described in Table 3.

TABLE 3

|  | First compound | Second compound | Initiator |
| --- | --- | --- | --- |
| Comparative Example 1 | — | Compound 203 (90.90% by weight), trimethylol propane triacrylate (4.79% by weight) | TPO (4.31% by weight) |
| Comparative Example 2 | Compound 102 (1.94% by weight) | Compound 203 (95.15% by weight) | TPO (2.91% by weight) |

Viscosity of the composition for fabricating an organic film was measured using a Brookfield DE-II+Pro viscometer at 25° C., and the results are shown in Table 4 below.

TABLE 4

|  | Viscosity (cps) |
| --- | --- |
| Comparative Example 1 | 14 |
| Comparative Example 2 | 15 |

Example 2

A glass substrate on which 500 organic light-emitting devices were formed was prepared. A glass capping layer having a thickness of 800 Å was formed to cover the organic light-emitting devices, and LiF was deposited on the capping layer to form a protective layer.

Then, an organic light-emitting display apparatus was manufactured by preparing an encapsulation layer by forming:
i) a lower inorganic film having a thickness of 10,000 Å by depositing silicon oxynitride ($SiO_xN_y$) on the protective layer;
ii) an organic film having a thickness of 4 μm on the lower inorganic film using the composition of Example 1; and
iii) an inorganic film having a thickness of 7,000 Å on the organic film by depositing silicon nitride ($SiN_x$).

Comparative Example 3

An organic light-emitting display apparatus was manufactured in the same manner as in Example 2, except that the composition of Comparative Example 1 was used in the formation of the organic film, instead of the composition of Example 1.

Evaluation Example 1: Evaluation of Lifespan of Organic Light-Emitting Display Apparatus Initial states of screens of the organic light-emitting display apparatuses manufactured according to Example 2 and Comparative Example 3 were observed using a microscope, and states of the screens after being stored at 85° C. and in a relative humidity 85% for 240 hours and 500 hours were observed using the microscope. Then, the number of cells having black spots were counted, and the results are shown in Table 5 below.

TABLE 5

|  | 240 hours | 500 hours |
| --- | --- | --- |
| Example 2 | 500 cells 0% | 500 cells 0% |
| Comparative Example 3 | 500 cells 5% | 500 cells 30% |

Referring to Table 5, the organic light-emitting display apparatus according to Example 2 exhibited excellent lifespan characteristics due to high durability against oxygen plasma, as compared with the organic light-emitting display apparatus according to Comparative Example 3.

By way of summation and review, an organic light-emitting display apparatus including the organic light-emitting device may further include a driving transistor or a switching transistor. An organic light-emitting device may be deteriorated by oxygen and/or moisture, and a sealing member may further be applied to the organic light-emitting device.

As described above, according to the one or more of the above exemplary embodiments, the organic light-emitting display apparatus has high stability during the plasma process.

The embodiments may provide compositions for fabricating an organic film having high stability in a plasma process.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic film of an organic light-emitting display apparatus, the organic film including a polymer derived from a composition comprising a first compound that includes:
   n substituents Y, and
   m polymerizable groups $P_1$,
   wherein:
   n is selected from 1, 2, 3, and 4;
   m is selected from 1, 2, 3, and 4;
   $OP_1$ of the first compound is equal to or greater than 2.8 and equal to or less than 4.8;
   $OP_1$ being (total number of atoms of the first compound)/{(number of carbon atoms of the first compound)−(number of oxygen atoms of the first compound)};
   $RP_1$ of the first compound is equal to or greater than 0.01 and equal to or less than 0.46; $RP_1$ being {(number of carbon atoms of the substituent Y)·n}/(number of carbon atoms of the first compound),
   wherein Y is selected from an unsubstituted $C_6$ aryl group, a substituted or unsubstituted $C_{10}$-$C_{60}$ aryl group, an unsubstituted $C_6$ aryloxy group, a substituted or unsubstituted $C_{10}$-$C_{60}$ aryloxy group, an unsubstituted $C_6$ arylthio group, and a substituted or unsubstituted $C_{10}$-$C_{60}$ arylthio group.

2. The organic film as claimed in claim 1, wherein m is selected from 1, 2, and 3.

3. The organic film as claimed in claim 1, wherein $P_1$ is selected from an acrylate group, an epoxy group, and a vinyl group.

4. The organic film as claimed in claim 1, wherein $P_1$ is a group represented by one of the following Formulae 6-1 to 6-3:

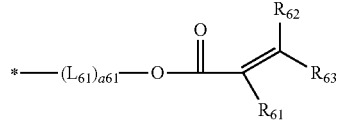

Formula 6-1

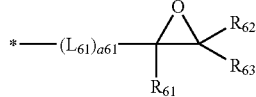

Formula 6-2

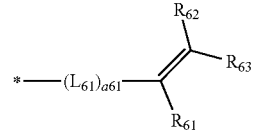

Formula 6-3 wherein, in Formulae 6-1 to 6-3,
$L_{61}$ is selected from a substituted or unsubstituted $C_1$-$C_{10}$ alkylene group and a substituted or unsubstituted $C_2$-$C_{10}$ alkenylene group;
a61 is selected from 0, 1, 2, 3, 4, and 5;
$R_{61}$ to $R_{63}$ are each independently selected from hydrogen, a substituted or unsubstituted $C_1$-$C_{10}$ alkyl group, and a substituted or unsubstituted $C_1$-$C_{10}$ alkoxy group; and
* is a binding site with an adjacent atom.

5. The organic film as claimed in claim 1, wherein the first compound is represented by one of the following Formulae 1-1, 1-2, 2-1, and 2-2:

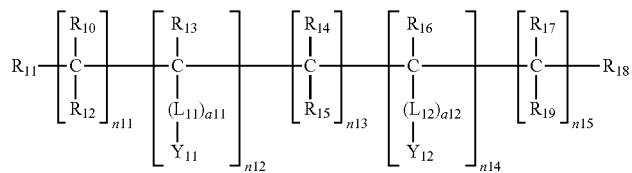

Formula 1-1

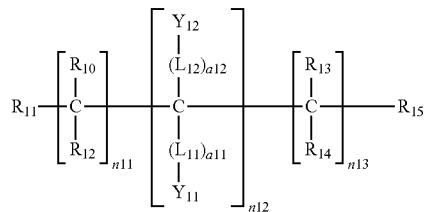

Formula 1-2

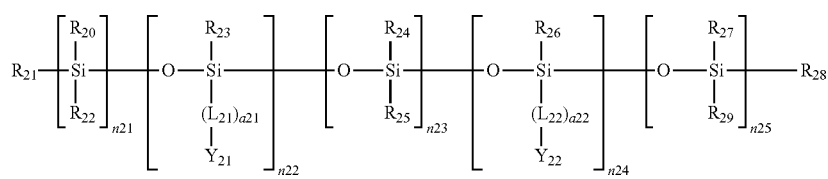

Formula 2-1

Formula 2-2

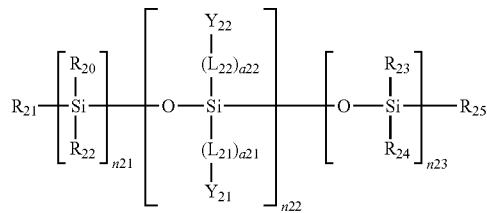

wherein, in Formulae 1-1, 1-2, 2-1, and 2-2, $Y_{11}$, $Y_{12}$, $Y_{21}$, and $Y_{22}$ are each independently selected from an unsubstituted $C_6$ aryl group, a substituted or unsubstituted $C_{10}$-$C_{60}$ aryl group, an unsubstituted $C_6$ aryloxy group, a substituted or unsubstituted $C_{10}$-$C_{60}$ aryloxy group, an unsubstituted $C_6$ arylthio group, and a substituted or unsubstituted $C_{10}$-$C_{60}$ arylthio group;

$L_{11}$, $L_{12}$, $L_{21}$, and $L_{22}$ are each independently selected from a substituted or unsubstituted $C_1$-$C_{10}$ alkylene group and a substituted or unsubstituted $C_2$-$C_{10}$ alkenylene group;

a11, a12, a21, and a22 are each independently selected from 0, 1, and 2;

$R_{10}$ to $R_{19}$ and $R_{20}$ to $R_{29}$ are each independently selected from hydrogen, deuterium, a substituted or unsubstituted $C_1$-$C_{10}$ alkyl group, a substituted or unsubstituted $C_3$-$C_{10}$ cycloalkyl group, and a polymerizable group $P_1$, wherein at least one of $R_{10}$ to $R_{19}$ is the polymerizable group $P_1$ and at least one of $R_{20}$ to $R_{29}$ is the polymerizable group $P_1$;

n11 to n15 and n21 to n25 are each independently selected from 0, 1, 2, 3, 4, and 5;

a sum of n12 and n14 is 1 or 2; and a sum of n22 and n24 is 1 or 2.

6. The organic film as claimed in claim 1, wherein the first compound is represented by one of the following Formulae 1-11 to 1-18 and 2-11 to 2-18:

Formula 1-11

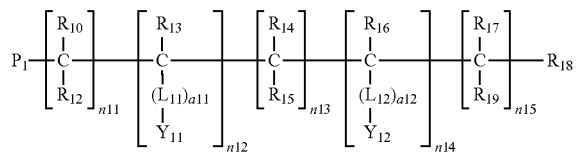

Formula 1-12

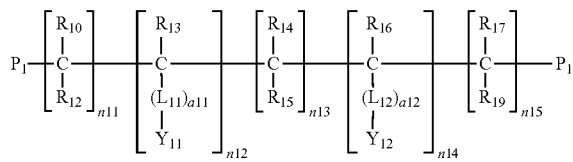

Formula 1-13

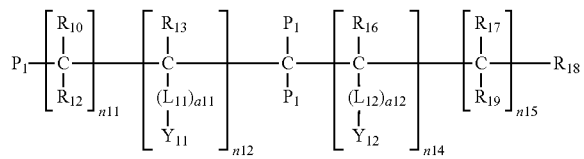

Formula 1-14

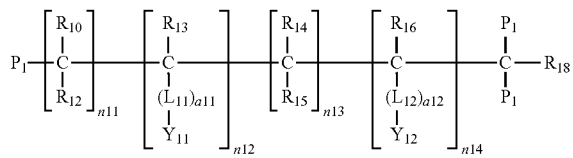

Formula 1-15

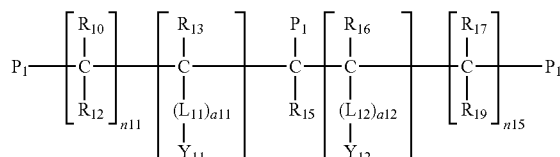

Formula 1-16

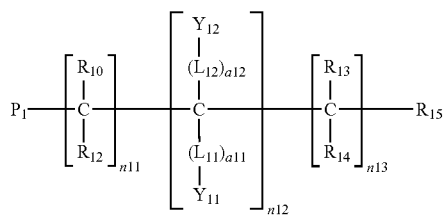

Formula 1-17

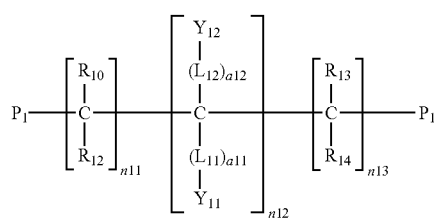

Formula 1-18

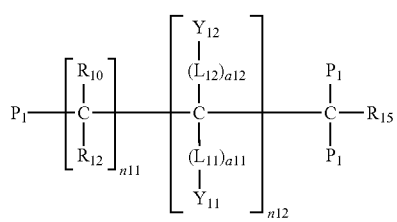

-continued

Formula 2-11
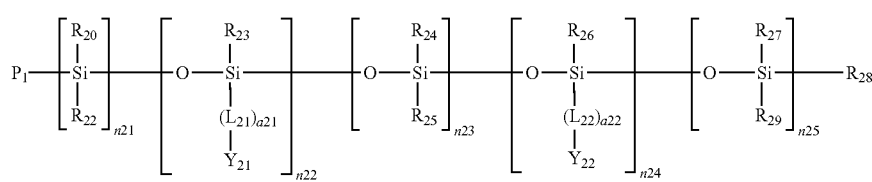

Formula 2-12
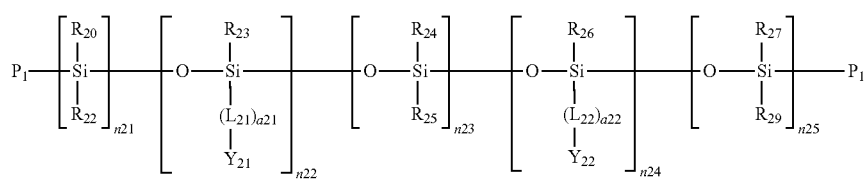

Formula 2-13
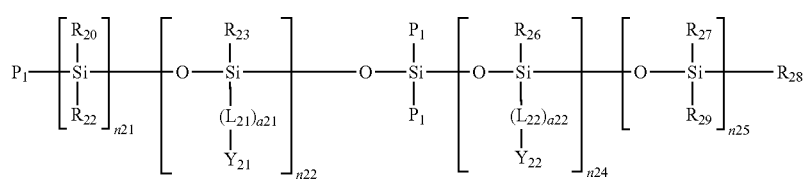

Formula 2-14
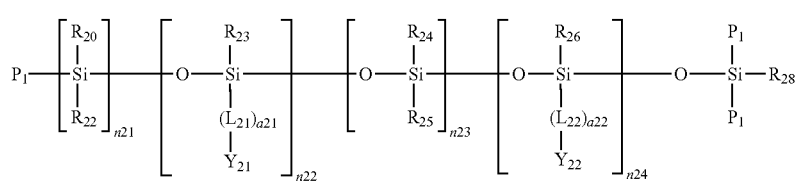

Formula 2-15
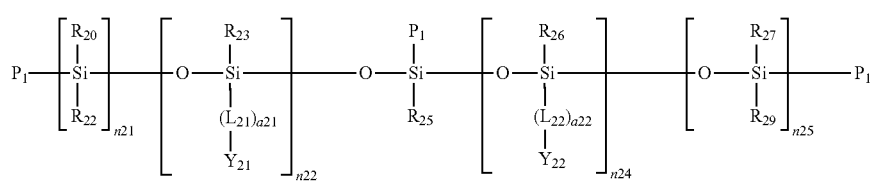

Formula 2-16
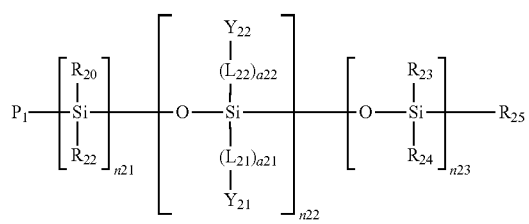

Formula 2-17
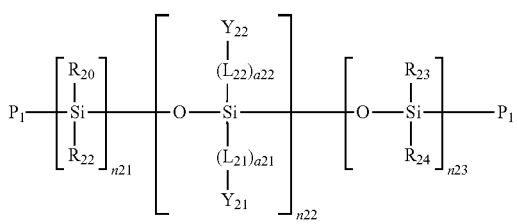

Formula 2-18
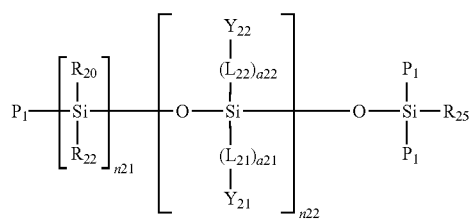

wherein, in Formulae 1-11 to 1-18 and 2-11 to 2-18, $Y_{11}$, $Y_{12}$, $Y_{21}$, and $Y_{22}$ are each independently selected from an unsubstituted $C_6$ aryl group, a substituted or unsubstituted $C_{10}$-$C_{60}$ aryl group, an unsubstituted $C_6$ aryloxy group, a substituted or unsubstituted $C_{10}$-$C_{60}$ aryloxy group, an unsubstituted $C_6$ arylthio group, and a substituted or unsubstituted $C_{10}$-$C_{60}$ arylthio group;

$L_{11}$, $L_{12}$, $L_{21}$, and $L_{22}$ are each independently selected from a substituted or unsubstituted $C_1$-$C_{10}$ alkylene group and a substituted or unsubstituted $C_2$-$C_{10}$ alkenylene group;

a11, a12, a21, and a22 are each independently selected from 0, 1, and 2;

$R_{10}$ to $R_{19}$ and $R_{20}$ to $R_{29}$ are each independently selected from hydrogen, deuterium, a substituted or unsubstituted $C_1$-$C_{10}$ alkyl group, and a substituted or unsubstituted $C_3$-$C_{10}$ cycloalkyl group;

$P_1$ is a group represented by one of the following Formulae 6-1 to 6-3;

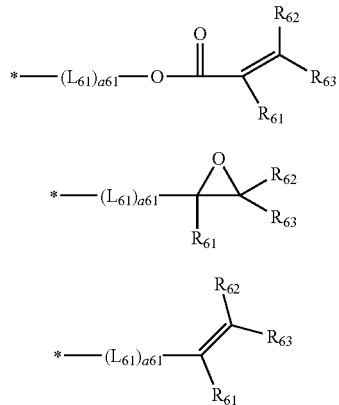

wherein, in Formulae 6-1 to 6-3, $L_{61}$ is selected from a substituted or unsubstituted $C_1$-$C_{10}$ alkylene group and a substituted or unsubstituted $C_2$-$C_{10}$ alkenylene group;

a61 is selected from 0, 1, 2, and 3;

$R_{61}$ to $R_{63}$ are each independently selected from hydrogen, a substituted or unsubstituted $C_1$-$C_{10}$ alkyl group, and a substituted or unsubstituted $C_1$-$C_{10}$ alkoxy group;

* is a binding site with an adjacent atom;

n11 to n15 and n21 to n25 are each independently selected from 0, 1, 2, 3, 4, and 5;

a sum of n12 and n14 is 1 or 2; and a sum of n22 and n24 is 1 or 2.

7. The organic film as claimed in claim 1, wherein the first compound is one of the following Compounds 101 to 106:

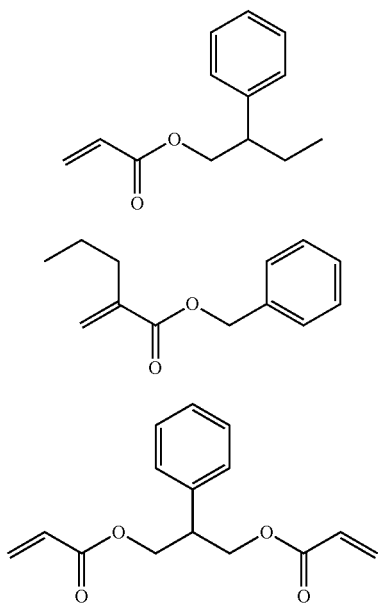

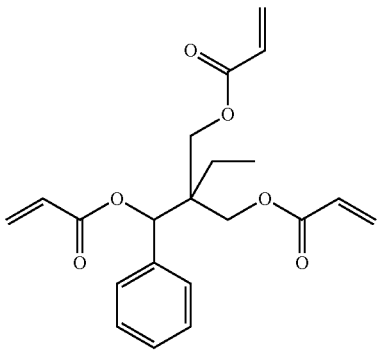

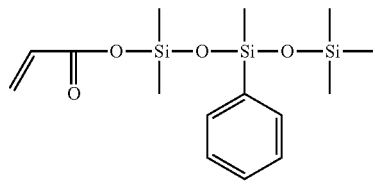

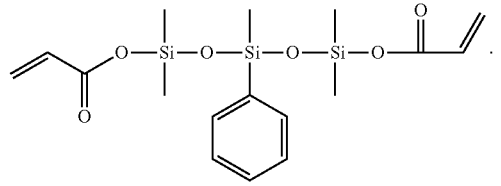

8. The organic film as claimed in claim 1,
wherein the composition further includes a second compound, and
wherein:
OP of the composition for fabricating an organic film is equal to or greater than 2.8 and equal to or less than 4.8; OP being $(n_1 \cdot OP_1 + n_2 \cdot OP_2)$;
RP of the composition for fabricating an organic film is equal to or greater than 0.01 and equal to or less than 0.46; RP being $n_1 \cdot RP_1$;
$n_1$ is (number of moles of the first compound)/(number of moles of the first compound+number of moles of the second compound);
$n_2$ is (number of moles of the second compound)/(number of moles of the first compound+number of moles of the second compound);
$OP_1$ is (total number of atoms of the first compound)/{(number of carbon atoms of the first compound)−(number of oxygen atoms of the first compound)};
$RP_1$ is {(number of carbon atoms of the substituent Y)·n}/(number of carbon atoms of the first compound); and
$OP_2$ is (total number of atoms of the second compound)/{(number of carbon atoms of the second compound)−(number of oxygen atoms of the second compound)}.

9. The organic film as claimed in claim 1, wherein the composition further includes an initiator.

10. The organic film as claimed in claim 1, wherein a viscosity of the composition is about 1 cps to about 100 cps at 25° C.

11. An organic light-emitting display apparatus, comprising:
a substrate;
an organic light-emitting device on the substrate; and
an encapsulation layer on the organic light-emitting device;

wherein the encapsulation layer includes 1, 2, or 3 sealing units, each sealing unit including an organic film and an inorganic film that are sequentially stacked on the organic light-emitting device;

the organic film includes a polymer prepared from a composition for fabricating an organic film that includes a first compound; the first compound including:

n substituents Y, n being selected from 1, 2, 3, and 4, and m polymerizable groups $P_1$, m being selected from 1, 2, 3, and 4;

wherein:

$OP_1$ of the first compound is equal to or greater than 2.8 and equal to or less than 4.8;

$RP_1$ of the first compound is equal to or greater than 0.01 and equal to or less than 0.46;

$OP_1$ is (total number of atoms of the first compound)/{(number of carbon atoms of the first compound)−(number of oxygen atoms of the first compound)};

$RP_1$ is {(number of carbon atoms of the substituent Y)·n}/(number of carbon atoms of the first compound); and Y is selected from an unsubstituted $C_6$ aryl group, a substituted or unsubstituted $C_{10}$-$C_{60}$ aryl group, an unsubstituted $C_6$ aryloxy group, a substituted or unsubstituted $C_{10}$-$C_{60}$ aryloxy group, an unsubstituted $C_6$ arylthio group, and a substituted or unsubstituted $C_{10}$-$C_{60}$ arylthio group.

12. The organic light-emitting display apparatus as claimed in claim 11, wherein:

the composition for fabricating an organic film further includes a second compound, OP of the composition for fabricating an organic film is equal to or greater than 2.8 and equal to or less than 4.8, OP being ($n_1 \cdot OP_1 + n_2 \cdot OP_2$);

RP of the composition for fabricating an organic film is equal to or greater than 0.01 and equal to or less than 0.46, RP being $n_1 \cdot RP_1$;

$n_1$ is (number of moles of the first compound)/(number of moles of the first compound+number of moles of the second compound);

$n_2$ is (number of moles of the second compound)/(number of moles of the first compound+number of moles of the second compound);

$OP_1$ is (total number of atoms of the first compound)/{(number of carbon atoms of the first compound)−(number of oxygen atoms of the first compound)};

$RP_1$ is {(number of carbon atoms of the substituent Y)·n}/(number of carbon atoms of the first compound); and $OP_2$ is (total number of atoms of the second compound)/{(number of carbon atoms of the second compound)−(number of oxygen atoms of the second compound)}.

13. The organic light-emitting display apparatus as claimed in claim 11, wherein the inorganic film includes at least one selected from metal, metal nitride, metal oxide, metal oxynitride, silicon nitride, silicon oxide, and silicon oxynitride.

14. The organic light-emitting display apparatus as claimed in claim 11, wherein the encapsulation layer further includes a lower inorganic film interposed between the organic light-emitting device and the organic film.

15. The organic light-emitting display apparatus as claimed in claim 11, further comprising at least one selected from a capping layer and a protective layer interposed between the organic light-emitting device and the encapsulation layer.

16. An organic film of an organic light-emitting display apparatus, the organic film including a polymer derived from a composition comprising a first compound that includes:

n substituents Y, and m polymerizable groups $P_1$, wherein:

n is selected from 1, 2, 3, and 4;

m is selected from 1, 2, 3, and 4;

$OP_1$ of the first compound is equal to or greater than 2.8 and equal to or less than 4.8;

$OP_1$ being (total number of atoms of the first compound)/{(number of carbon atoms of the first compound)−(number of oxygen atoms of the first compound)};

$RP_1$ of the first compound is equal to or greater than 0.01 and equal to or less than 0.46; $RP_1$ being {(number of carbon atoms of the substituent Y)·n}/(number of carbon atoms of the first compound); and wherein the first compound include silicon atom.

17. The organic film as claimed in claim 16, further comprising a second compound, wherein:

OP of the composition for fabricating an organic film is equal to or greater than 2.8 and equal to or less than 4.8; OP being ($n_1 \cdot OP_1 + n_2 \cdot OP_2$);

RP of the composition for fabricating an organic film is equal to or greater than 0.01 and equal to or less than 0.46; RP being $n_1 \cdot RP_1$;

$n_1$ is (number of moles of the first compound)/(number of moles of the first compound+number of moles of the second compound);

$n_2$ is (number of moles of the second compound)/(number of moles of the first compound+number of moles of the second compound);

$OP_1$ is (total number of atoms of the first compound)/{(number of carbon atoms of the first compound)−(number of oxygen atoms of the first compound)};

$RP_1$ is {(number of carbon atoms of the substituent Y)·n}/(number of carbon atoms of the first compound); and $OP_2$ is (total number of atoms of the second compound)/{(number of carbon atoms of the second compound)−(number of oxygen atoms of the second compound)}.

* * * * *